(12) United States Patent
Coppeta et al.

(10) Patent No.: US 8,317,507 B1
(45) Date of Patent: Nov. 27, 2012

(54) SYSTEMS FOR MAKING MICROTABLETS FOR DRUG DELIVERY

(75) Inventors: Jonathan R. Coppeta, Windham, NH (US); Robert Dyer, Concord, MA (US); Cynthia L. Stevenson, Mountain View, CA (US)

(73) Assignee: On Demand Therapeutics, Inc., Tyngsboro, MA (US)

( * ) Notice: Subject to any disclaimer, the term of this patent is extended or adjusted under 35 U.S.C. 154(b) by 0 days.

(21) Appl. No.: 13/469,115

(22) Filed: May 11, 2012

Related U.S. Application Data

(62) Division of application No. 13/365,722, filed on Feb. 3, 2012, now Pat. No. 8,192,659.

(60) Provisional application No. 61/533,397, filed on Sep. 12, 2011.

(51) Int. Cl.
*B29C 43/02* (2006.01)

(52) U.S. Cl. ......... 425/253; 425/346; 425/351; 425/352

(58) Field of Classification Search .................. None
See application file for complete search history.

(56) References Cited

U.S. PATENT DOCUMENTS

| | | | |
|---|---|---|---|
| 4,134,943 A | 1/1979 | Knitsch et al. | |
| 4,542,835 A | 9/1985 | Gamberini | |
| 4,965,027 A | 10/1990 | Takahashi | |
| 5,549,144 A | 8/1996 | Dworak et al. | |
| 5,556,771 A | 9/1996 | Shen et al. | |
| 5,683,721 A | 11/1997 | Perovitch et al. | |
| 7,354,597 B2 | 4/2008 | Johnson et al. | |
| 7,449,342 B2 | 11/2008 | Kane et al. | |
| 2001/0042317 A1 | 11/2001 | Yarborough et al. | |
| 2004/0146434 A1 | 7/2004 | Kane et al. | |
| 2005/0145291 A1 | 7/2005 | Ede et al. | |
| 2007/0259348 A1 | 11/2007 | Phadke et al. | |
| 2009/0162435 A1 | 6/2009 | Bunick et al. | |
| 2010/0330149 A1 | 12/2010 | Daniel et al. | |

FOREIGN PATENT DOCUMENTS

| | | |
|---|---|---|
| WO | 9609815 A1 | 4/1996 |
| WO | 2010125087 A1 | 11/2010 |

OTHER PUBLICATIONS

Kane, et al., System for Dispensing Sub-Milligram Doses of Active Pharmaceutical Powders for Early Stage Solubility Assays, JALA 9(4): 218-227, Aug. 2004.

Dale, et al., Pressure-Induced Activity Loss in Solid State Catalase, J. Pharmaceutical Sciences, vol. 84, No. 2, 190-193, Feb. 1995.

Imamura, et al., Influence of compression of water sorption, glass transition,and enthalpy relaxation behavior of freeze-dried amorphous sugar matrices, International Journal of Pharmaceutics 408 (2011) 76-83.

(Continued)

*Primary Examiner* — Mary F Thisen
(74) *Attorney, Agent, or Firm* — Sutherland Asbill & Brennan LLP

(57) ABSTRACT

Methods and systems are provided for making a drug microtablet. The method includes loading a lyophilization capillary channel with a liquid drug solution; lyophilizing the liquid drug solution in the lyophilization capillary channel to produce a lyophilized drug formulation; compressing the lyophilized drug formulation in the lyophilization capillary channel, or in a compression capillary channel, to form a microtablet; and ejecting the microtablet from the lyophilization capillary channel or compression capillary channel. The methods and systems may provide drug microtablets having improved content uniformity and reduced weight variability.

20 Claims, 15 Drawing Sheets

OTHER PUBLICATIONS

Teng et al., The Effect of Compactional Pressure on Urease Activity, Pharmaceutical Research, vol. 5, No. 12, 1988.

Kuny, et al., Compression behavior of the enzyme B-galactosidase and its mixture with microcrystalline cellulose, International Journal of Pharmaceutics, 260 (2003) 137-147.

Pinto, Evaluation of the Potential Use of Poly(ethylene oxide) as Tablet- and Extrudate-Forming Material, AAPS PharmSci 2004; 6 (2) Article 15 (http://www.aapspharmsci.org).

Mini-Tabs, Investigation of Mini-Tab Capsule Filling Using a Zanasi Lab 16 Machine, Colorcon, pp. 1-5.

Vuong, et al., The Influence of In Vitro Dissolution Method on Lansoprazole release from Enteric Coated Mini-Tabs, Colorcon Limited, www.colorcon.com/about/contact Controlled Release Study Annual Meeting 2009.

Vuong, et al, Evaluation of the Enteric Performance of Lansoprazole Mini-Tabs Coated in a Perforated Pan, Colorcon Limited, www.colorcon.com/about/contact, Modified Release, American Association of Pharmaceutical Scientists Annual Meeting Nov. 2008.

Vuong, et al., Investigation of Enteric Coating of Mini-Tabs Using a Perforated Pan or a Fluid-Bed Machine, Colorcon Limited, www.colorcon.com/about/contact, Modified Release, Controlled Release Society Annual Meeting, Jul. 2008.

Picker, Influence of tableting on the enzymatic activity of different a-amylases using various excipients, European J. Pharmaceutics and Biopharmaceutics 53 (2002) 181-185.

International Search Report and Written Opinion for International Application No. PCT/US12/50244 dated Oct. 9, 2012.

Plug of powder being punched and dispensed into a micro well plate.

US 8,317,507 B1

SYSTEMS FOR MAKING MICROTABLETS FOR DRUG DELIVERY

CROSS-REFERENCE TO RELATED APPLICATIONS

This application is a divisional of U.S. application Ser. No. 13/365,722, filed Feb. 3, 2012, which claims benefit of U.S. Provisional Application No. 61/533,397 filed Sep. 12, 2011, the disclosures of which are incorporated herein by reference.

BACKGROUND

This disclosure generally relates to microtablets for drug delivery and to methods of making microtablets which comprise a drug. In particular, the disclosure relates to methods for making microtablets in a process that is readily scalable and that produces consistent microtablets.

Solid forms of drug may be desirable for many reasons, including formulations with low moisture content that allow increased in vivo drug stability in implantable drug delivery systems, and the ability to provide highly concentrated drug formulation, which may be required for small implants (which need an efficacious drug payload in a small volume). However, the preparation and handling of small amounts of drug can present challenges in maintaining consistency and reproducibility of the drug formulation.

U.S. Patent Application Publication No. 2004/0146434, published on Jul. 29, 2004, and Kane et al., *JALA* 9(4): 218-227, published August 2004, describe one example of methods and systems for the preparation and handling of small amounts of solids, which generally involves forming a powder bed, inserting a tube into the powder bed to obtain a "plug" of powder, removing the tube from the bed, and ejecting the plug of powder. (See Kane et al., and FIG. 1 of this patent application). Such prior art methods, however, may suffer problems, including difficulty reproducibly forming small amounts of solids having consistent therapeutic dosages. Numerous factors contribute to these difficulties, including non-homogeneous/non-uniform powder beds, powder bed integrity during the coring process, changing powder bed boundary conditions due to adjacent coring, inefficient use of the formulation (e.g., only ~50% of powder bed surface area can be cored), and deleterious effects (on both powder properties {flow properties, density, compressibility, agglomeration} and drug stability) of recycled powder beds and/or previously compressed powder beds on formation of subsequent plugs. One of the smallest tableting dosage forms available using commercially available equipment is provided by Colorcon Inc. Mini-Tabs are ~2 mm in diameter and can be enterically coated using perforated pan or fluid bed coating technology.

A method for manufacturing tablets smaller than 1-2 mm, with good reproducibility and content uniformity, has not yet been achieved. Furthermore, tableting biomolecules (regardless of tablet size) using conventional techniques without the loss of activity is not readily achievable.

Thus, a need exists for methods and systems for making microtablets of solid drug formulations for drug delivery that desirably overcome one or more of the foregoing problems associated with prior methods. There also is a need for such a process that can be scaled to increase production of microtablets without deleterious effects on the product specifications, such as content uniformity.

SUMMARY

In one aspect, methods are provided for making one or more drug microtablets. In one embodiment, the method includes (i) loading a lyophilization capillary channel with a liquid drug solution; (ii) lyophilizing the liquid drug solution in the lyophilization capillary channel to produce a lyophilized drug formulation; (iii) compressing the lyophilized drug formulation in the lyophilization capillary channel to form a microtablet; and (iv) ejecting the microtablet from the lyophilization capillary channel. In an alternative embodiment, the lyophilized drug formulation is transferred from the lyophilization capillary channel to a compression capillary channel before being compressed to form the microtablet. The compression capillary channel may be slightly larger than the lyophilization capillary channel to facilitate ease of transferring and tableting of the lyophilized drug formulation.

In particular, the methods are readily scalable for making a plurality of microtablets, for example simultaneously. Such plurality of microtablets advantageously may be characterized as having reduced weight variability and/or as having improved content uniformity.

In another aspect, systems are provided for making a drug microtablet. In one embodiment, the systems includes a capillary tooling system having a lyophilization capillary channel; a liquid dispensing device operable to load a liquid drug solution into the lyophilization capillary channel; a freeze-dryer operable to lyophilize the liquid drug solution in the lyophilization capillary channel and produce a lyophilized drug formulation therein; and a compression device operable to compress the lyophilized drug formulation in the lyophilization capillary channel to form a microtablet. In an alternative embodiment, the system includes a separate compression capillary channel and a transfer mechanism for moving the lyophilized drug formulation from the lyophilization capillary channel to the compression capillary channel, and the compression device is instead operable to compress the lyophilized drug formulation in the compression capillary channel to form the microtablet. The systems preferably include an array of multiple capillary channels so that a plurality of microtablets can be produced simultaneously.

DETAILED DESCRIPTION

Figure 1:
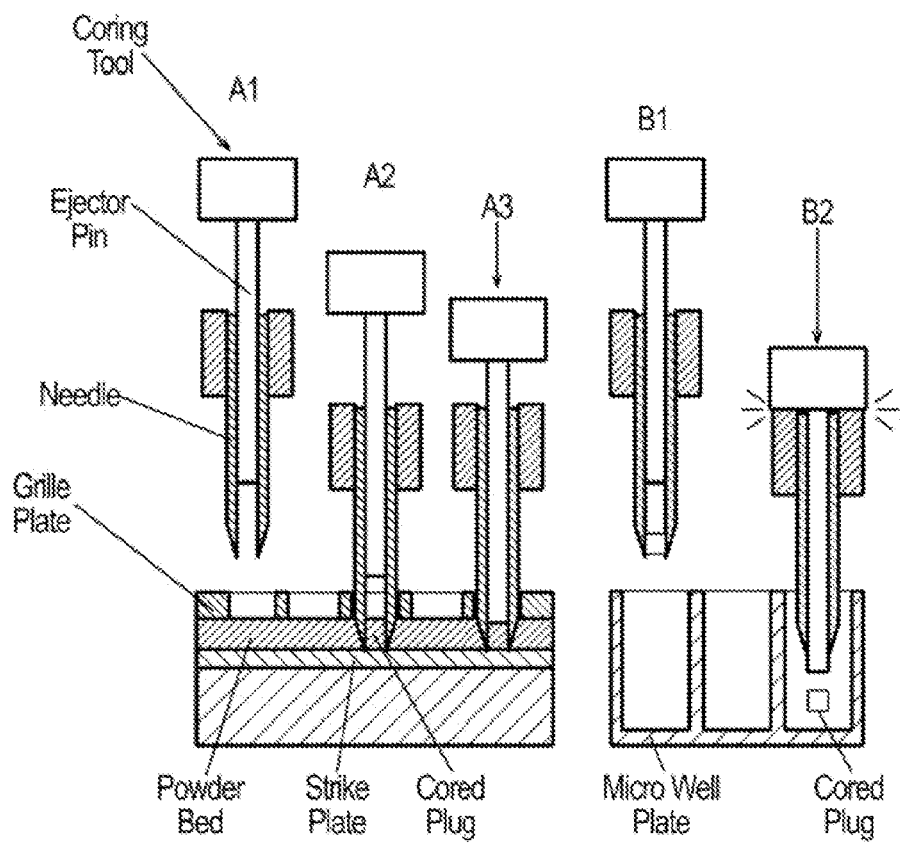
FIG. 1 is a schematic illustration of a prior art coring method for forming small tablets.

Improved methods and systems for preparing drug microtablets have been developed. The methods and systems are particularly well suited for forming drug microtablets that include sensitive protein and other macromolecule drugs. The methods and systems provide drug stability and pharmacokinetic advantages as compared to conventional tableting techniques and advantageously enable the manufacture of microtablets using a scalable, rapid, and possibly automated process for production of microtablets. The process advantageously avoids or minimizes the transfer and handling of powders, and it avoids the difficulties associated with the measurement of microscale volumes of solid powder by instead relying on more accurate, reproducible liquid volume measurements. In one embodiment, the process requires no transfer of drug powder between lyophilization and tableting equipment. Accordingly, the processes described herein advantageously can produce microtablets having a reduced weight variability and improved content uniformity compared to known conventional tableting or microtableting processes.

As used herein, the terms "capillary channel" refers to an enclosed passage, usually tubular, having an aperture, or through-hole, having a cross-sectional dimension (e.g., diameter) up to 2000 µm, such as between about 100 µm and 1000 µm, and having an aspect ratio of at least 1, such as between 10 and 100. The capillary channel may be referred to as the "bore" of a capillary tube.

A "microtablet," as used herein, refers to a shaped unit of compressed powder having a size of 2000 microns or less in the longest dimension. The shaped unit typically has regular shape, such as round, cubic, cylindrical, tapered cylinder, conical, spherical, or the like. The "drug microtablet" is a microtablet that comprises at least one active pharmaceutical ingredient (API), with or without one or more excipients.

In various embodiments, the microtablets will be less than 1500 microns, less than 1000 microns, less than 750 microns, or less than 500 microns, in the longest dimension.

"Reduced weight variability," as used herein, refers to microtablets having an actual weight that deviates less than about 10%, less than about 5%, less than about 2.5%, or less than about 1% of the target weight. These values would apply to total tablet weight and the drug content within the microtablet will also be ±10%.

"Improved content uniformity," as used herein, refers to microtablets having an active ingredient that differs from a target amount by less than about 25%, less than about 15%, less than about 10%, less than about 5%, or less than about 1% of the target amount. For example, if a target amount of an active ingredient of 100 micrograms is specified for a particular formulation, microtablets having improved content uniformity would have between about 75 micrograms to about 125 micrograms of active ingredient, between about 85 micrograms to about 115 micrograms of active ingredient, between about 90 micrograms to about 110 micrograms of active ingredient, between about 95 micrograms to about 105 micrograms of active ingredient, or between about 99 micrograms to about 101 micrograms of active ingredient. In a preferred embodiment, the present methods and systems provide microtablet preparations that conform to U.S. Food and Drug Administration specifications for content uniformity.

Embodiments of the methods and apparatus for making microtablets may be further understood by reference to the drawings, which illustrates non-limiting examples of methods and systems according to embodiments of the present invention.

A. Methods for Making Microtablets

In one embodiment, the method generally includes providing a capillary tooling system having at least one lyophilization capillary channel for receiving a liquid drug solution; filling the lyophilization capillary channel with the liquid drug solution; lyophilizing the liquid drug solution in the lyophilization capillary channel to obtain a lyophilized drug formulation; compressing the lyophilized drug formulation in the lyophilization capillary channel, or in a separate compression capillary channel, to form a microtablet; and thereafter ejecting the microtablet from the lyophilization capillary channel or compression capillary channel. In certain embodiments, the filling, lyophilizing, and compressing steps are performed in the lyophilization capillary channel. In other embodiments, the filling and lyophilizing steps are performed in the lyophilization capillary channel and the compressing step is performed in the compression capillary channel. In such other embodiments, the method further comprises transferring the lyophilized drug formulation directly or indirectly from the lyophilization capillary channel to the compression capillary channel before compressing the lyophilized drug formulation to form the microtablet.

In a preferred embodiment, the capillary tooling system comprises a plurality of capillary channels, which may be disposed in an array so that one or more of the filling, lyophilizing, compressing, and ejecting steps can be performed simultaneously in/on the plurality of capillary channels, in order to scale-up the number of microtablets produced per unit time. The array may comprise tens, hundreds, or thousands of capillary channels.

Figure 2A:
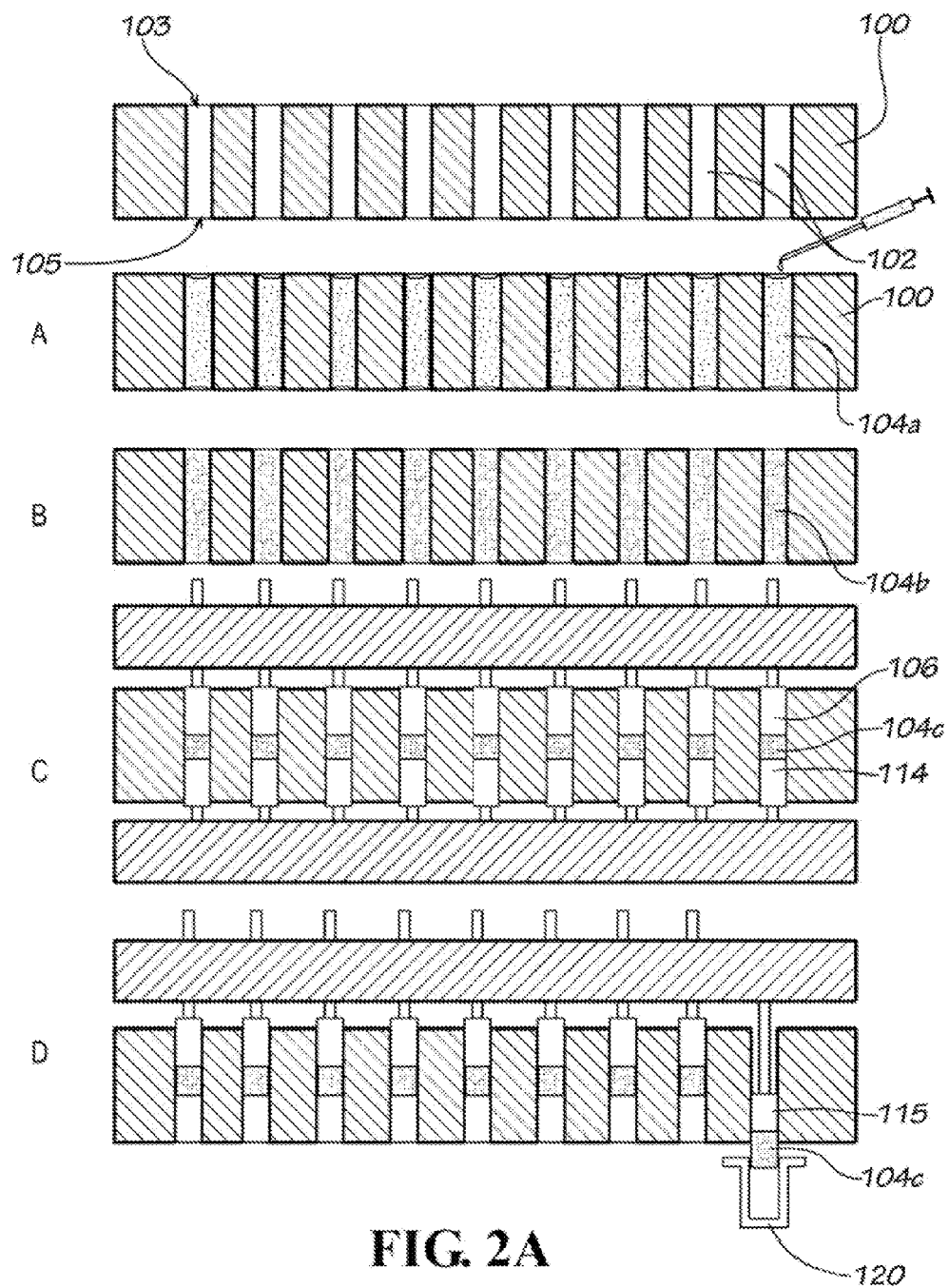
FIGS. 2A, 2B, and 2C are cross-sectional views of systems and methods for making microtablets according to three exemplary embodiments.

FIG. 2A shows the sequence of steps in one embodiment of the method, using a capillary tooling system 100 that includes an array of lyophilization capillary channels 102. Each channel has a first opening 103 and an opposed second opening 105. In the method, the capillary channels 102 are each filled with a selected quantity of a liquid drug solution 104a (shown as step A). Then, the liquid drug solution in the capillary channel 102 is lyophilized to produce a lyophilized drug formulation 104b (shown as step B). In this step, solvent and other volatile components of the liquid drug solution are removed, leaving a solid drug formulation, i.e., the lyophilized drug formulation. Next, the lyophilized drug formulation 104b is compressed by pistons 106 and 114 in the lyophilization capillary channels 102 to form microtablets 104c (shown as step C). Finally, the microtablets 104c are ejected from the lyophilization capillary channels 102 (shown as step D). In this embodiment, the microtablets 104c are ejected using pistons 115. Piston 106 and piston 115 may be the same piston. In FIG. 2A, one of the microtablet 104c is shown being ejected directly into a device 120.

Figure 2B:
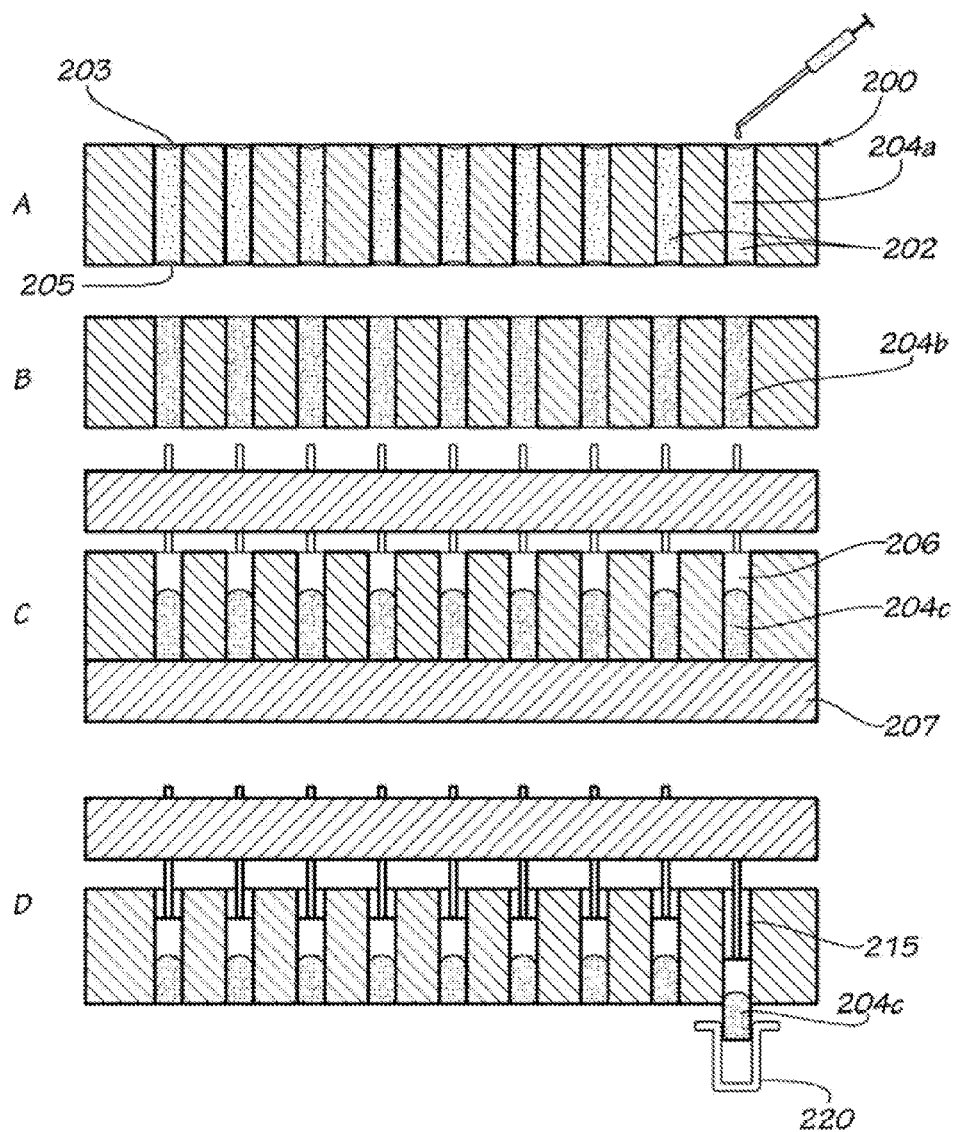

FIG. 2B shows the sequence of steps in another embodiment of the method, using a capillary tooling system 200 that includes an array of lyophilization capillary channels 202. Each channel 202 has a first opening 203 and an opposed second opening 205. In the method, the capillary channels 202 are each filled with a selected quantity of a liquid drug solution 204a (shown as step A). Then, the liquid drug solution in the capillary channel 202 is lyophilized to produce a lyophilized drug formulation 204b (shown as step B). Next, the lyophilized drug formulation 204b is compressed from one side with pistons 206 inserted into the first opening 203 of the lyophilization capillary channels 202 against strike plate 207 positioned adjacent to the second opening 205 of the lyophilization capillary channels 202 to form microtablets 204c (shown as step C). Finally, the microtablets 204c are ejected from the lyophilization capillary channels 202 (shown as step D). In this embodiment, the microtablets 204c are ejected using pistons 215. Piston 206 and piston 215 may be the same piston. In FIG. 2B, one of the microtablet 104c is shown being ejected directly into a device 220.

Figure 2C:
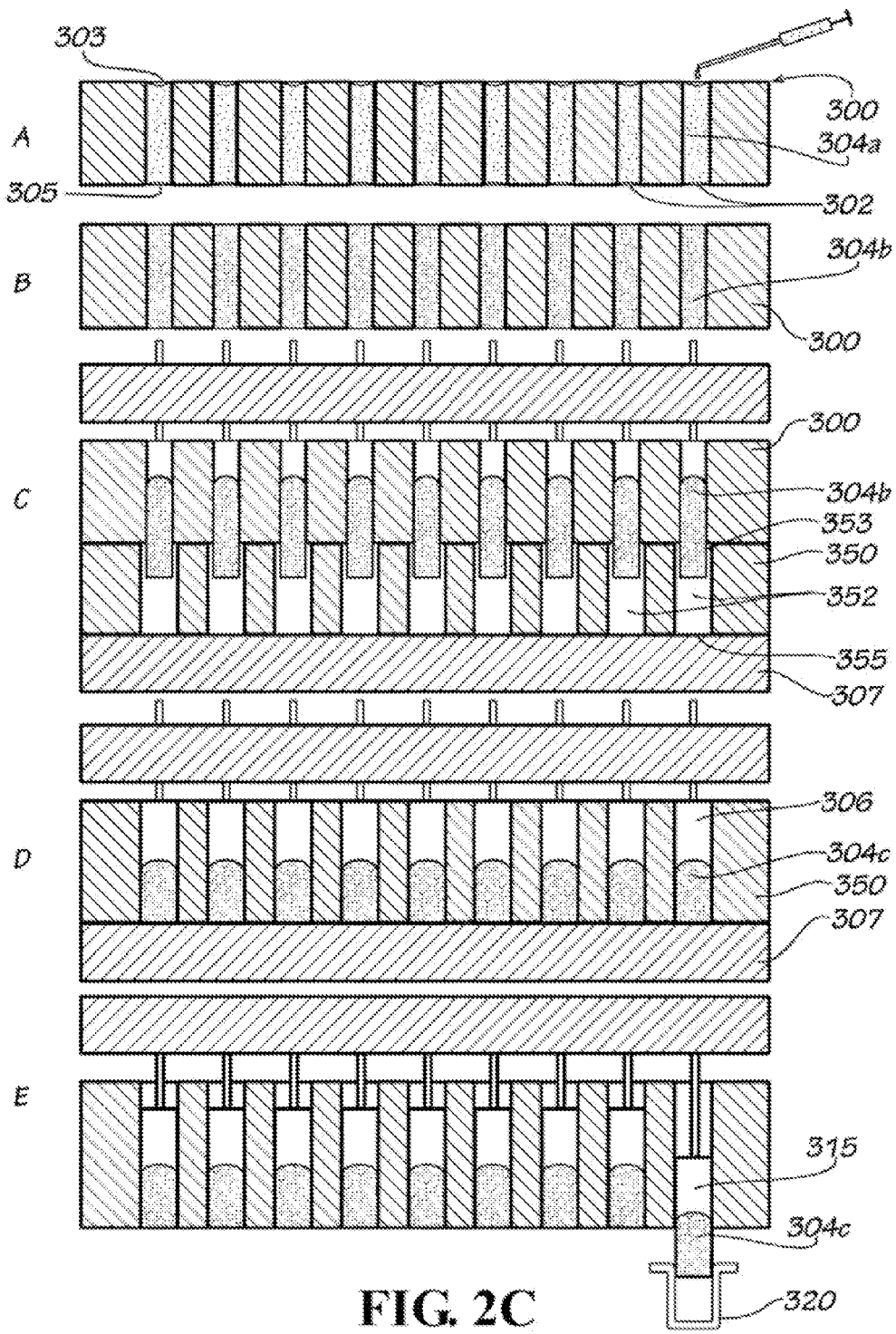

The steps of filling and lyophilizing and the steps of compressing and ejecting may be conducted in the same capillary channels, as shown in FIGS. 2A and 2B. Alternatively, the steps of filling and lyophilizing may be conducted in a first capillary channel, with the steps of compressing/tableting and ejecting conducted in a second capillary channel, such as one having a larger diameter than the first capillary channel. FIG. 2C illustrates an embodiment of such an alternative method.

FIG. 2C shows the sequence of steps in another embodiment of the method, using a capillary tooling system 300 that includes an array of lyophilization capillary channels 302. Each channel 302 has a first opening 303 and an opposed second opening 305. In the method, the capillary channels 302 are each filled with a selected quantity of a liquid drug solution 304a (shown as step A). Then, the liquid drug solution in the capillary channel 302 is lyophilized to produce a lyophilized drug formulation 304b (shown as step B). Next, the capillary tooling system 300 is positioned adjacent to a compression tooling system 350 with the lyophilization capillary channels 302 aligned with compression capillary channels 352, so that opening 305 is in communication with the opening 353 of compression capillary channel 352. Subsequently, the lyophilized drug formulation 304b is transferred into compression capillary channel 352 (shown as step C) and then compressed from one side with pistons 306 inserted into opening 353 of the compression capillary channels 352 against strike plate 307 positioned adjacent to a second opening 355 of the compression capillary channels 352 to form microtablets 304c (shown as step D). Finally, the microtablets 304c are ejected from the compression capillary channels 352 (shown as step E). In this embodiment, the microtablets 304c are ejected using pistons 315. Piston 306 and piston 315 may be the same piston. In FIG. 2C, one of the microtablet 304c is shown being ejected directly into a device 320.

The size of the compression capillary channel 352 may be the same size, larger, or smaller than the lyophilization capillary channel 302. In a preferred embodiment, the compression capillary channel 352 has a diameter that is larger than the lyophilization capillary channel 302 in order to facilitate the transfer of the lyophilized drug formulation 304b from the lyophilization capillary channel 302 to the compression capillary channel 352. For example, the compression capillary channel may have a diameter that is from about 5% to about 75% greater than the lyophilization capillary channel. In various examples, the cross-section of the compression capillary channel is from 10% to 70% larger than that of the lyophilization capillary channel.

Any suitable method may be used to assist in transferring the lyophilized drug formulation 304b from the lyophilization capillary channel 302 to the compression capillary channel 352. For example, the lyophilized drug formulation may be transferred by gravity, mechanical force, or a positive or negative pressure differential, or a combination thereof. In one case, a piston is inserted into the channel to drive out the formulation. In another case, a fluid pressure or vacuum is applied to the one of the openings in the compression capillary channel to drive out the formulation. Transferring the lyophilized drug formulation from the lyophilization capillary channel to the compression capillary channel is believed to mitigate binding of the drug formulation to the capillary bore wall, thereby enhancing breakup and compression of the cake structure of the lyophilized drug formulation to form the microtablet.

The lyophilization capillary channel of the capillary tooling system may be filled with the liquid drug solution using any suitable filling means. For example, in certain embodiments the capillary channel may be filled using a micropipette, needle and syringe, nano or micro droplet injector (e.g. BioDot systems), or other suitable means for transferring a precise amount (e.g., volume) of the liquid drug solution directly into the capillary. In other embodiments, the at least one capillary channel may be filled by drawing the liquid drug solution into the capillary channel by capillary forces (e.g., by wicking of the liquid drug solution). In such embodiments, an open end of the at least one capillary channel is exposed directly to the liquid drug solution, for example by bringing the solution into contact or close proximity to the open end of the capillary channel.

Providing a capillary tooling system and filling the capillaries with a precise volume of the liquid drug solution enables the preparation of a microtablets having both reduced weight variability and improved content uniformity as compared to conventional tableting methods and systems, such as those disclosed in Kane et al., *JALA* 9(4): 218-27 (2004). This is due at least in part to the technical feasibility of measuring very small liquid volumes and solution concentrations with substantial precision, which leads to better precision in meeting mass specifications than would generally be obtainable by handling and measuring very small dry powder volumes.

The liquid drug solution can be prepared using standard techniques. For example, the drug may be dissolved in a suitable organic or aqueous solvent or co-solvent system. The drug solution may be highly concentrated (e.g., 40% solids) in order to achieve small liquid capillary dimensions and shorten lyophilization times. The liquid formulation may be sterile filtered (0.22 µm) prior to lyophilization. The solvent or co-solvent system may comprise water and/or a volatile organic solvent known in the art.

Lyophilization of the liquid drug solution is performed using techniques known in the art therefor, including the use of known equipment and control systems for manipulating the liquid drug solution and surrounding atmosphere. In one embodiment, the lyophilization cycle has both primary drying (removal of frozen water) and secondary drying (removal of bound water) stages, resulting in a substantially dry powder (preferably less than 1% residual moisture) remaining in the capillaries. The resulting lyophilized drug formulation may be in a fluffy powder form.

The compression, or tableting step, of the process follows the lyophilization step. The compression step preferably is done in controlled environment, with or without an intervening transfer step to move the lyophilized drug formulation into a second capillary channel, i.e., transferring the lyophilized drug formulation from a lyophilization capillary channel into a compression capillary channel. In a preferred embodiment, the compression includes application of a dynamic mechanical force effective to compress the lyophilized drug formulation into the form of a microtablet inside one of the capillary channels. The mechanical force may be applied by means of an actuator driving a piston inside the capillary channel.

The force required to compress the lyophilized drug formulation into a microtablet will vary depending on various factors, including the composition of the lyophilized drug formulation (including any necessary binders or release agents), the desired tablet density, and the desired friability of the microtablet. In certain embodiments, the step of compressing the lyophilized drug formulation comprises applying a predetermined force to the lyophilized drug formulation in the range of from about 1,000 to about 30,000 psi. The microtableting force may be applied in a single step or may be accomplished by using a series of steps. In embodiments, a sequential series of pistons having increasing diameters may be applied at an increasing force to pre-compact the microtablet prior to applying the final microtableting force. This technique may be used to prevent piston binding and to achieve a denser microtablet. The force may be applied for a brief period (such as 1 second) or a longer period (such as 10 seconds to 600 seconds) to provide additional time for the microtablet to consolidate.

In one embodiment, a force feedback system is used to achieve greater repeatability and control of the microtablet compression process. For example, piston force, pressure or displacement may be measured to achieve a desired microtablet size or compaction. Thus, in embodiments, the step of compressing the microtablets may further comprise controlling either the force or position of the actuator/piston used to apply the force and monitoring the other.

Other factors that also may influence the microtableting and that may be modified accordingly include the compression rate (linear or other), the design and material properties of the capillary tooling system components (such as the piston face, surface finish, and material), vibration, and process environment (such as temperature and humidity).

For example, in embodiments the method further comprises applying additional energy, such as thermal or vibration (such as tapping or ultrasonic vibration), to the piston and/or capillary tooling system before and/or during the microtableting process to aid in the consolidation process; however, it is believed that energy and tableting forces should be minimized to reduce the risk of damaging the drug, i.e., the active pharmaceutical ingredient (API).

In still further embodiments, the microtableting methods include controlling the process environment during the microtableting process. Means for controlling such conditions are known in the art and may be effective at controlling the exposure of the drug formulations, microtablets and/or the implantable drug delivery device into which the microtablets may be ejected during the process. That is, to limit or prevent exposure to microbes (sterility), water (humidity), air (oxygen), temperature and/or light. For example, in an embodiment all or a portion of the microtableting method may be conducted under an inert environment (substantially free of water and oxygen) using inert gases (such as nitrogen, argon, or helium), or under vacuum. The microtableting method also may be conducted by controlling the system temperature (such as by reducing the system temperature).

After the tablet is formed in the capillary channel, then the tablet is ejected from the capillary tube. In one embodiment, one or more microtablets may be ejected directly into a drug delivery device or component thereof. In an embodiment, the microtablets are ejected and inserted into a reservoir, such as a microreservoir, of an implantable drug delivery device. Multi-reservoir drug delivery devices for implantation into a patient for controlled drug delivery are known in the art. The reservoir subsequently may be sealed, such as by hermetic sealing techniques known in the art or described in U.S. Application No. 61/522,219, filed Aug. 10, 2011, which is incorporated herein by reference.

The microtablets may be ejected from the capillaries using any suitable technique. For example, in embodiments the ejecting the microtablet from the capillary channel includes application of a piston, vibration, a pressurized fluid, or a combination thereof to the microtablet. The capillary channel may also be oriented to use gravity to facilitate microtablet ejection.

Figure 4A:
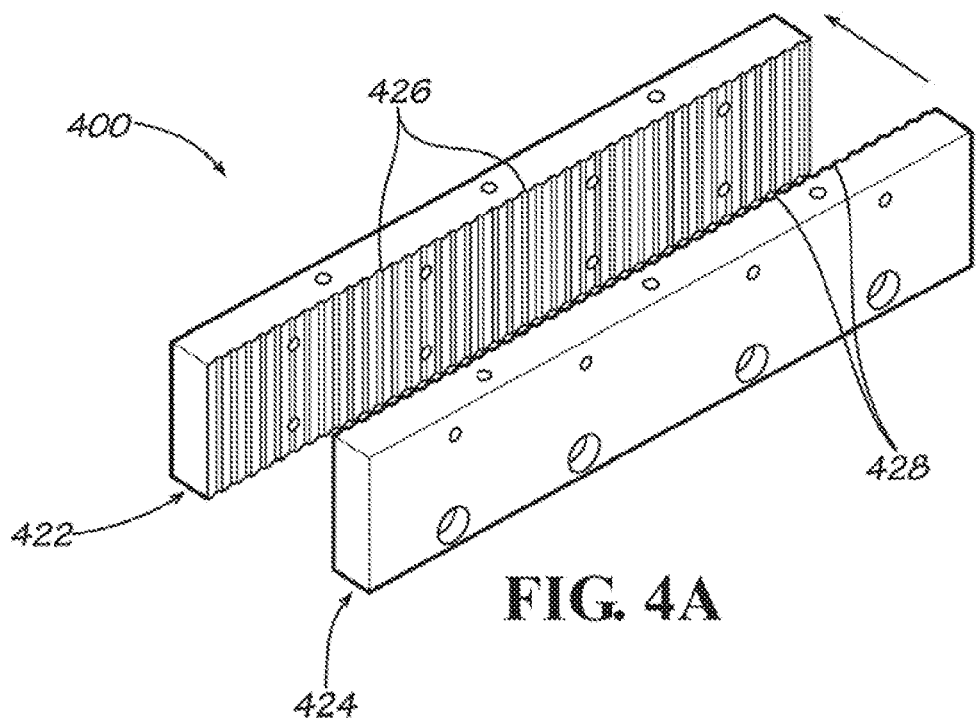
FIGS. 4A and 4B are perspective views of a capillary tooling system according to an embodiment.
Figure 4B:
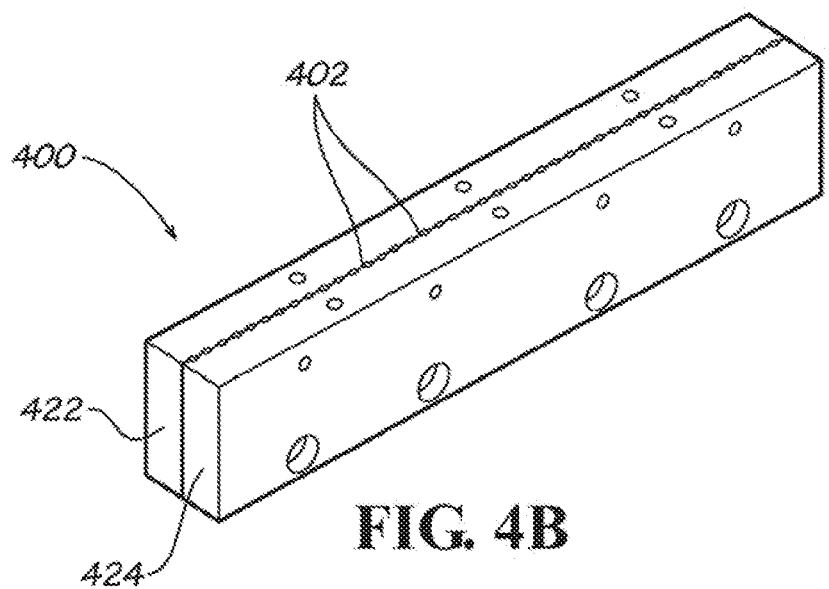
Figure 4C:
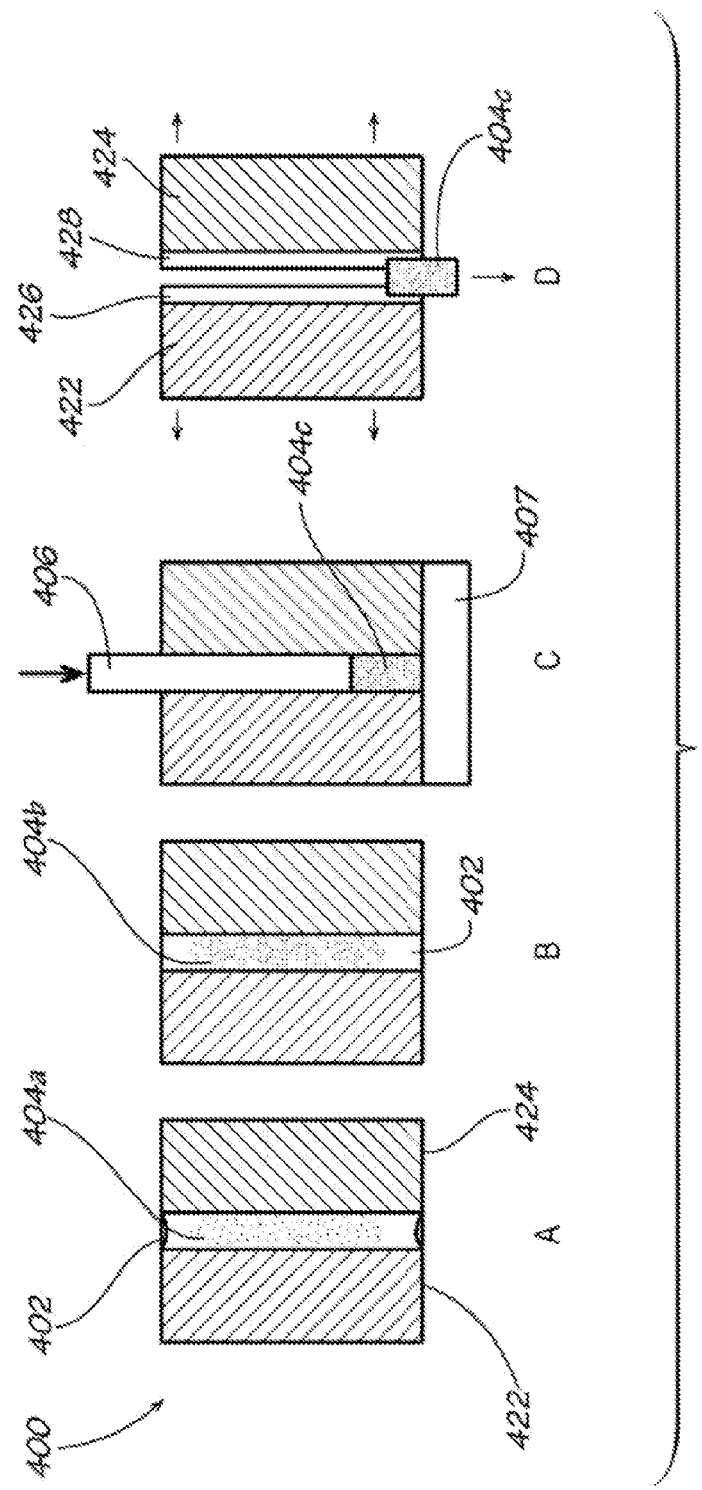
FIG. 4C is a schematic, in a cross-sectional view, of a method for preparing microtablets using capillary tooling system of FIGS. 4A and 4B.
Figure 5A:
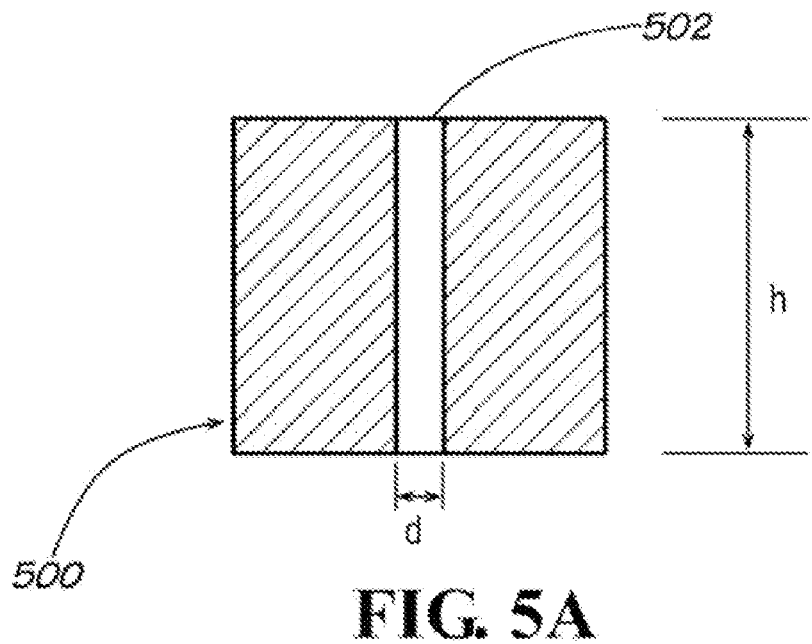
FIGS. 5A and 5B are cross-sectional views of capillary channels according to two embodiments.
Figure 5B:
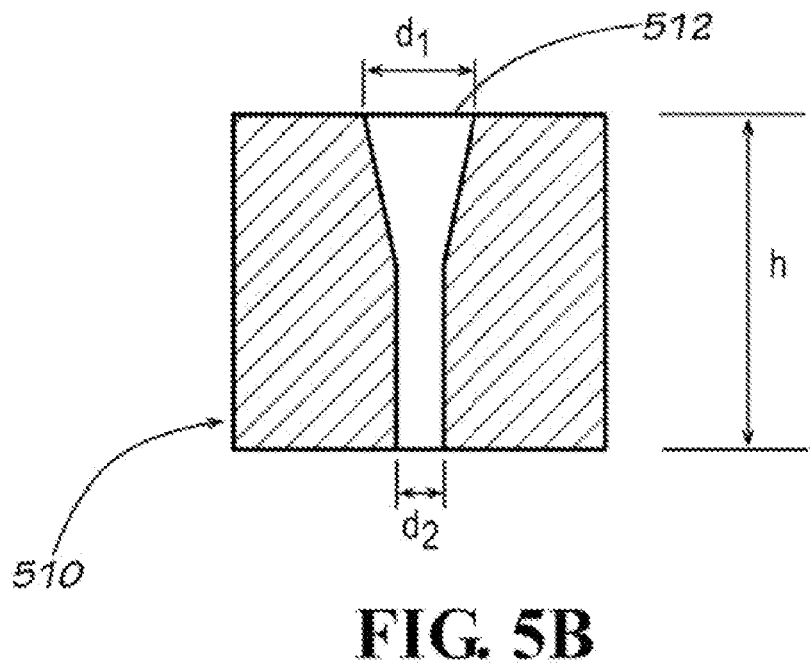

In one embodiment, which is illustrated in FIGS. 4A-4C, the step of ejecting the microtablet includes unmating (i.e., separating) two components of a capillary tooling, in which each capillary channel is defined by two separable components, to release a microtablet formed therein.

The ejection of the microtablet from the capillary can be done at any appropriate time. For example, the microtablet may be ejected substantially immediately (i.e., within 1 second) following the compression of the lyophilized drug formulation to obtain the microtablet or the microtablet may be held in the capillary for a predetermined time prior to its ejection to provide protection, storage and/or contribute to the compaction of the microtablet.

In one embodiment, the microtableting methods and systems are conducted with minimal or no handling of the drug formulation or microtablets during the processing. For example, the method may include a processing means for automating the capillary filling, lyophilizing, compressing, and ejecting (i.e., microtablet transfer) in a sterile, controlled atmosphere. Such means may include the use of various combinations of electromechanical or pneumatic actuators, microprocessors, pumps, conveyors, power systems, and other automation equipment and methods, which are well known in the art.

B. Systems for Making Microtablets

Figure 6:
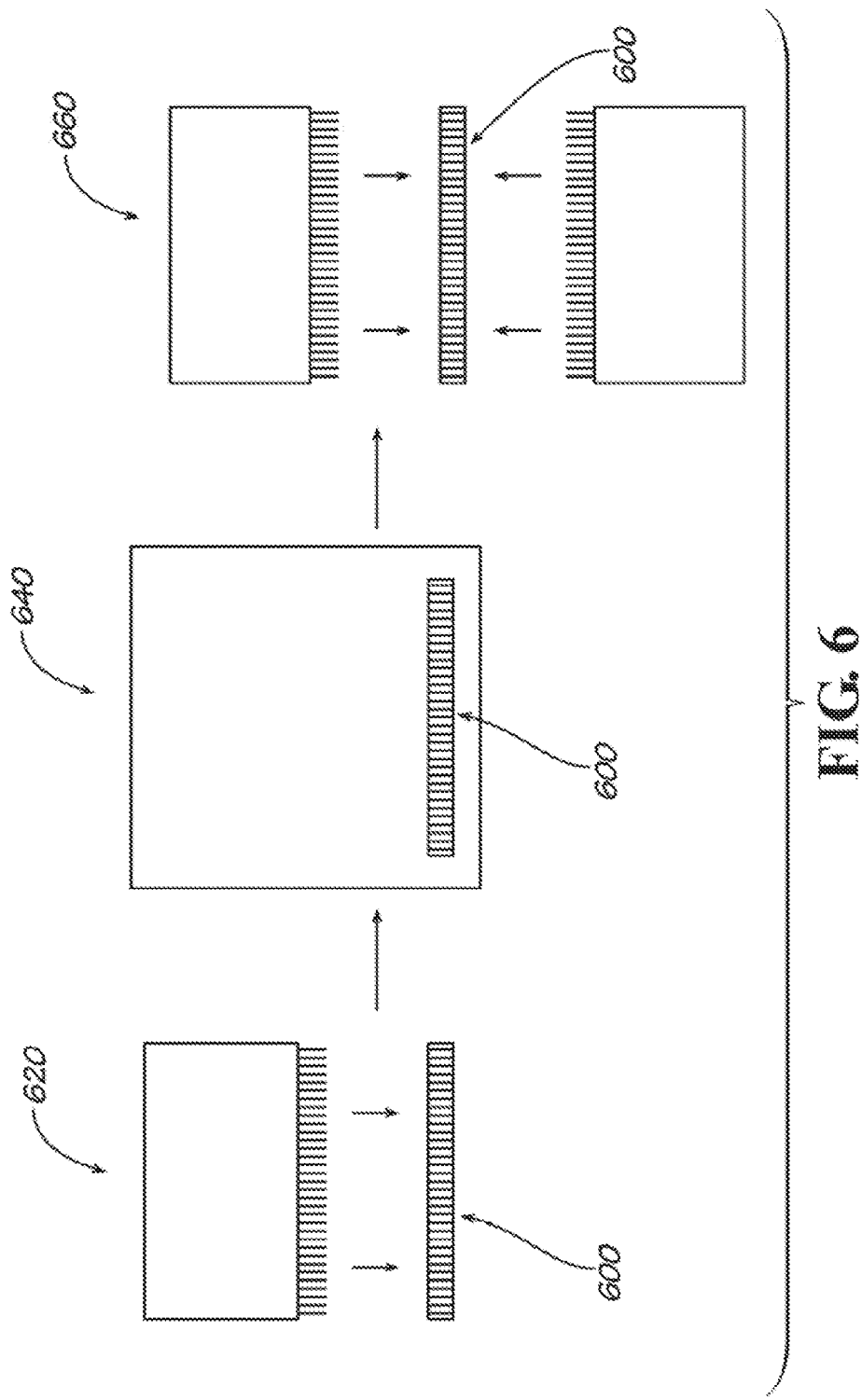
FIG. 6 is a schematic illustration of a system for preparing microtablets according to an embodiment.
Figure 7A:
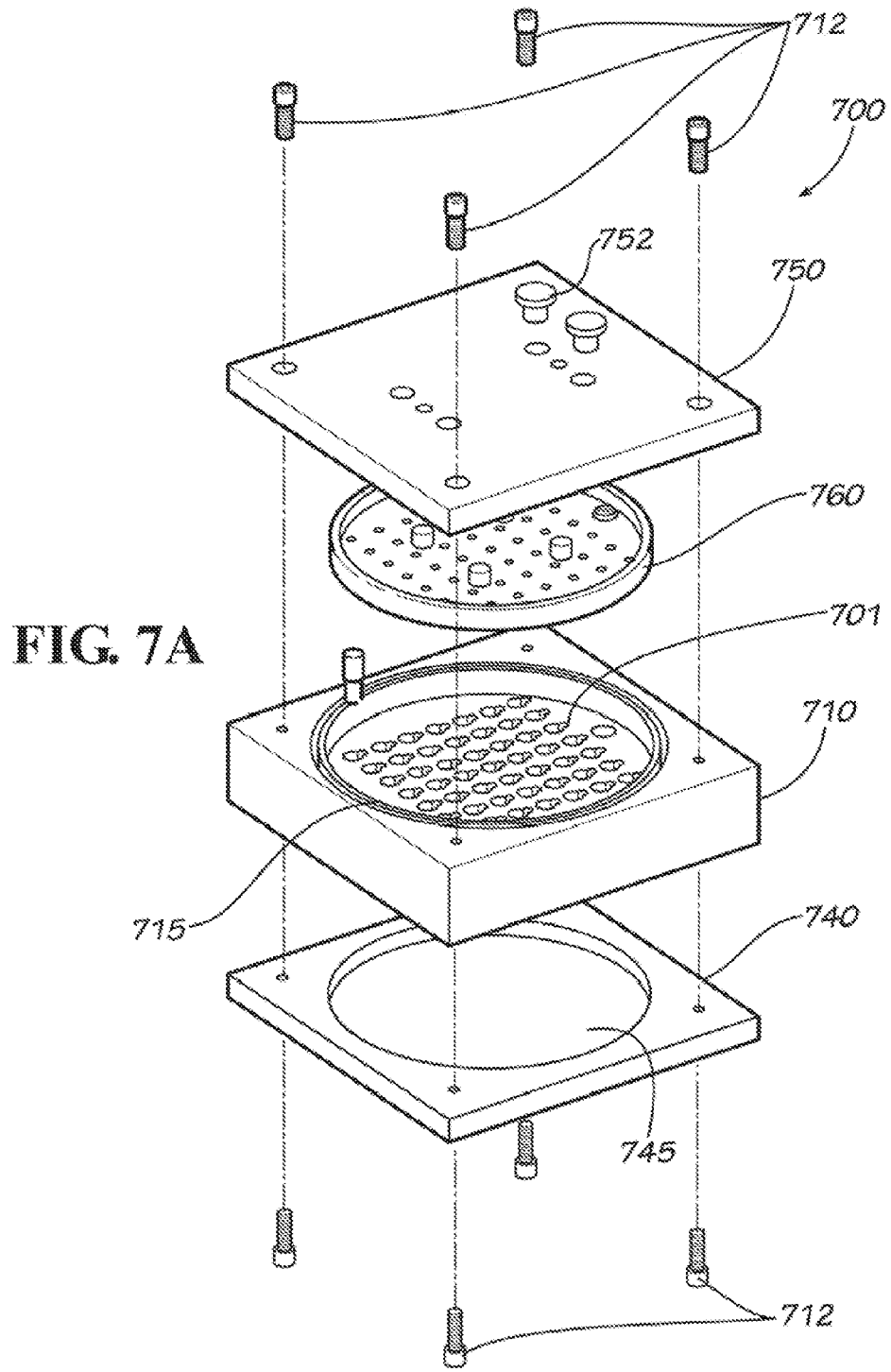
FIGS. 7A and 8A are exploded perspective views of a capillary tooling system according to two embodiments.
Figure 7B:
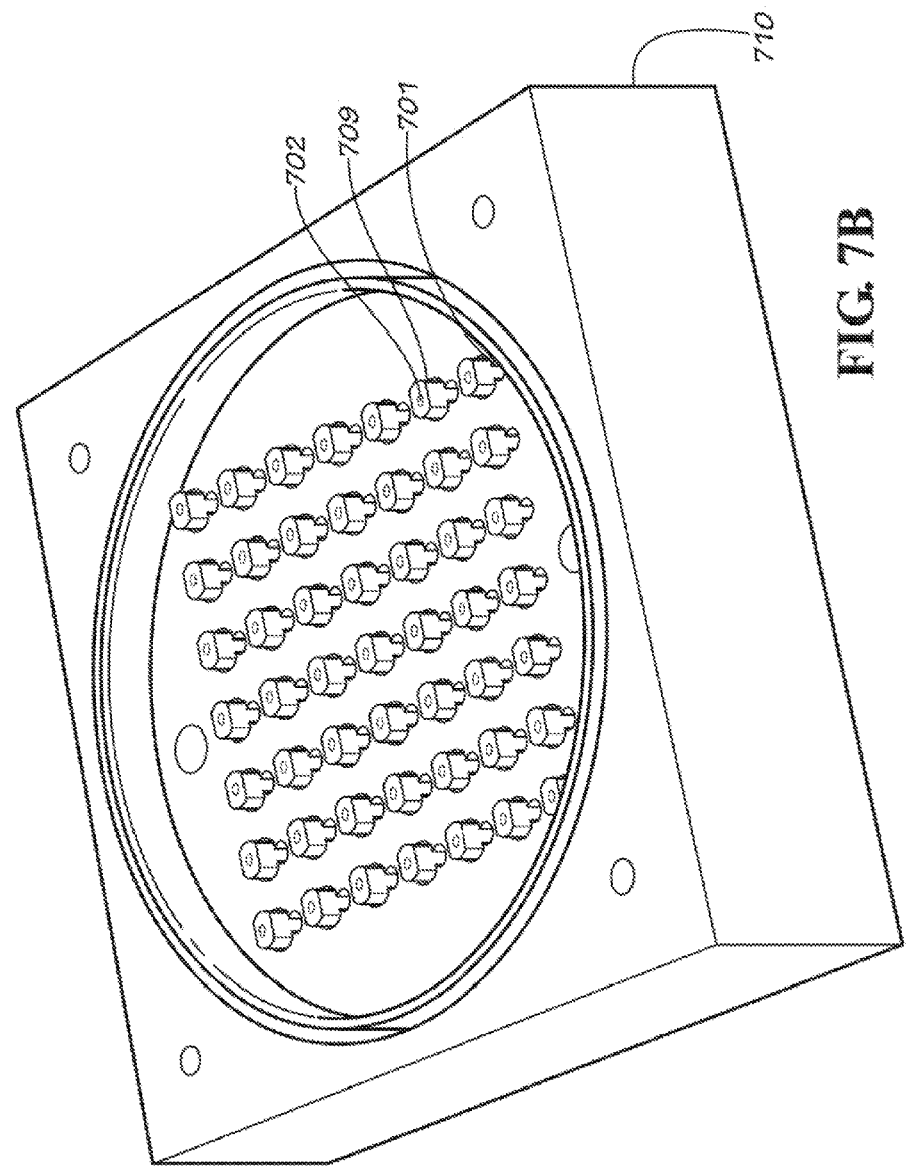
FIGS. 7B and 8B are perspective views of the capillary tooling systems of FIGS. 7A and 8A, respectively.

Systems for performing the microtableting methods described herein may include new combinations of new tooling and new or conventional mechanical, electromechanical, and computer control systems. Generally, in one embodiment, which is illustrated in FIG. 6, the microtableting system includes a capillary tooling system 600 having a plurality of capillary channels; a filling system 620 suitable for filling the capillary channels with a liquid drug solution; a lyophilization system 640 for lyophilizing the liquid drug solution to produce a lyophilized drug formulation; and compression system 660 for converting the lyophilized drug formulation into microtablets within the capillary channels of the tooling system. The microtableting system may also include a separate system (not shown) for ejecting the microtablets from the capillary channels if the compression system is not also configured to eject the microtablets. In another embodiment (not shown), the microtableting system further includes a second capillary tooling system comprising compression capillary channels and mechanisms for transferring the lyophilized drug formulation from the lyophilization capillary channels into the compression capillary channels.

Capillary Tooling System

Various embodiments of capillary tooling systems, or parts thereof, are illustrated in FIGS. 4-8. One embodiment is shown in FIGS. 7A and 7B, illustrating a tooling system 700 that includes a tooling base 710 having a plurality of wells 701 into which a plurality of glass and/or metal capillary tubes 709 with capillary channels 702 are disposed. FIG. 7A also shows other components of a suitable tooling system, including a lyophilization base 740 and lyophilization lid 750 that are secured on opposing sides of the tooling base 700 with screws 712. O-ring 715 is disposed between the tooling base 710 and lyophilization lid 706. A second O-ring is (not shown) is disposed between the tooling base 740 and 710. The lyophilization lid 750 and lyophilization base 740 are configured to allow solvent (e.g., water) from the liquid drug formulation to egress from both open ends of the capillary channels 702 during the lyophilization process. For example, the lyophilization base 704 includes a depression 745, and a spacer 760 is positioned/dimensioned to provide gas egress between the capillary channel opening and the lyophilization base 740 and lyophilization lid 750. Such features improve the lyophilization efficiency and speed and may promote formation of a more uniform "cake" (i.e., the solid uncompressed lyophilized drug formulation).

The capillary tooling system 700 further includes lyophilization plugs 752 to seal the system so that the drug formulation has the environment of the last step of the lyophilization chamber upon removal of the tooling system from the lyophilization chamber. The lyophilization plugs 752 remain "up" during the lyophilization cycle and then are compressed into the seated position by the lyophilization system, a process that is routine with lyophilization of stoppered glass vials.

Figure 8A:
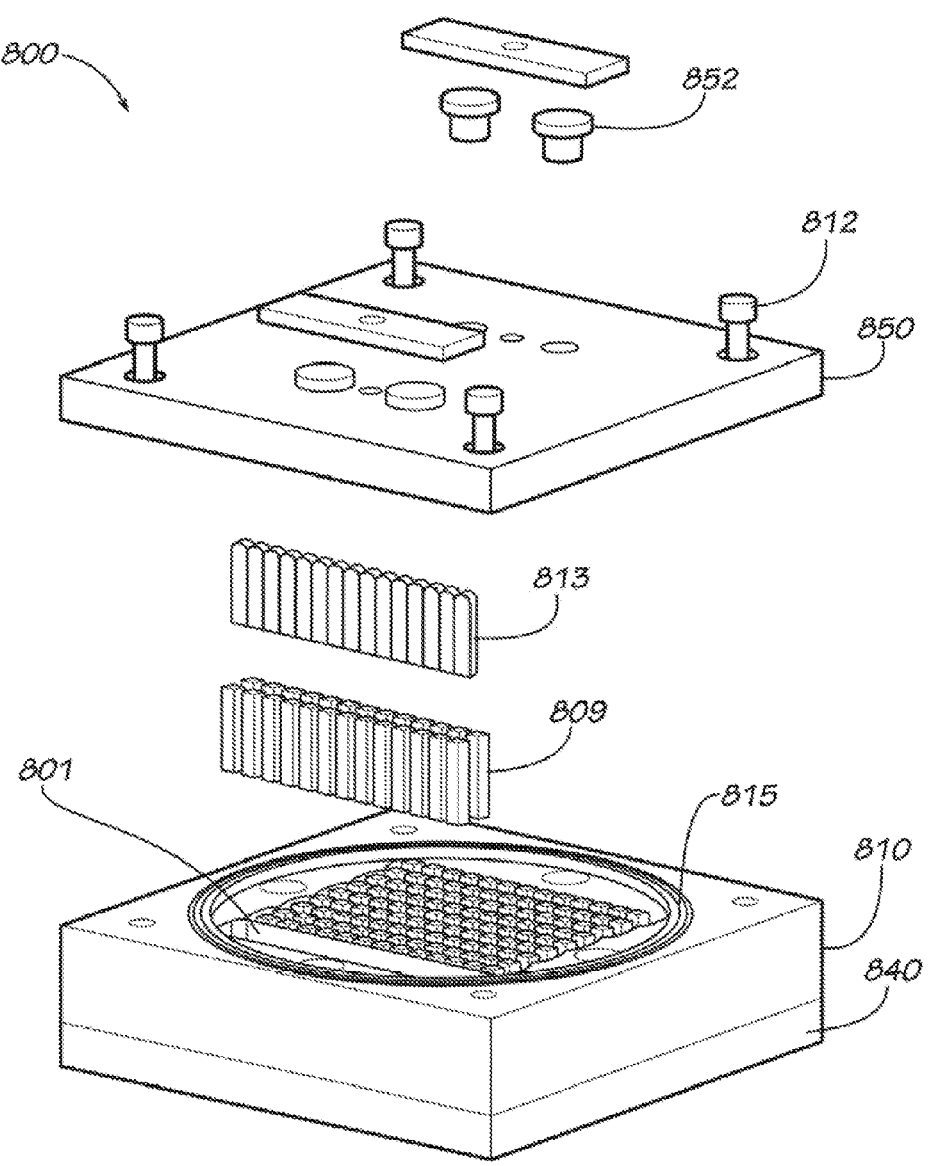
Figure 8B:
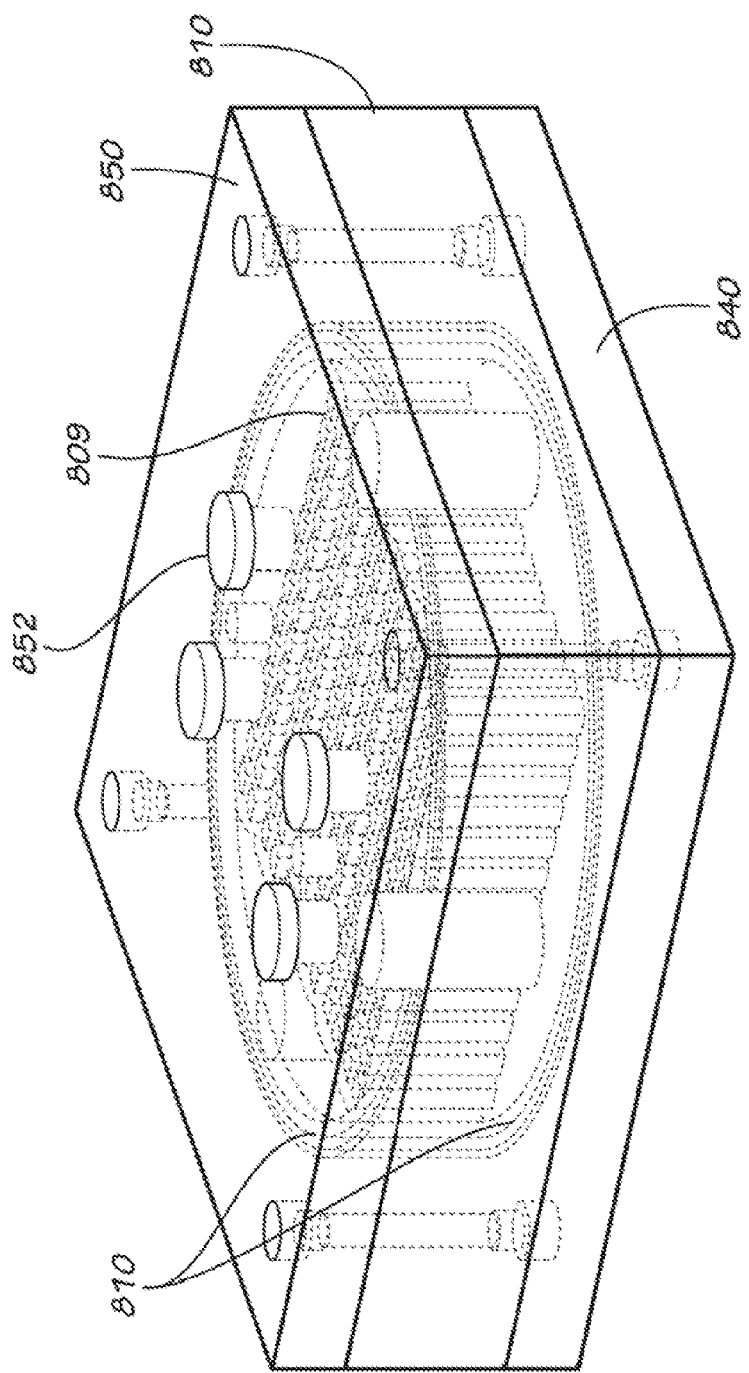

Another embodiment is shown in FIGS. 8A and 8B, illustrating a tooling system 800 that includes a tooling base 810 having a plurality of slots 801 in each of which are disposed one or more rows of glass or metal capillary tubes 809. Each capillary tube 809 has a capillary channel (not shown). The capillary tooling system 800 is configured and designed to enhance the heat transfer to/from the individual capillary tubes 809 by maintaining good thermal contact between the capillary tubes 809 and the tooling base 810 by including a spacer 813 disposed in the slot 801 between rows of capillary tubes 809 to secure the capillary tubes 809 against the walls of the slot 801, thereby improving the heat transfer between the tooling base 800 and the capillary tubes 809. Like tooling system 700, tooling system 800 also includes a lyophilization base 840 and lyophilization lid 850 which is secured to the tooling base 810 with screws 812, as well as O-ring 815 and lyophilization plugs 852 to seal the system.

FIGS. 4A and 4B illustrate an alternative embodiment of a capillary tooling base 400. It has two parts 422, 424 that mate together to define an array of capillary channels 402. That is, first part 422 has a mating face that has a plurality of straight, parallel, spaced grooves 426, each of which defines half of a capillary channel 402, and second part 424 has a mating face that has a matching plurality of straight, parallel, spaced grooves 428, each of which defines the other half of the capillary channel 402.

FIG. 4C illustrates a process of making a microtablet using capillary tooling base 400. In step A, parts 422 and 424 are mated and capillary channel 402 is filled with liquid drug solution 404a. In step B, the liquid drug solution is lyophilized in capillary channel 402 to produce a lyophilized drug formulation 404b. In step C, the lyophilized drug formulation is compressed in capillary channel 402 using piston 406 and strike plate 407 to form microtablet 404c. Finally, in step D, the parts 422 and 424 are unmated to separate channel 402 into grooves 426 and 428 and thereby facilitate ejection of microtablet 404c.

The capillary channels are sized and shaped to hold a selected volume of liquid drug solution. For example, in certain embodiments the capillaries have a diameter of about 0.3 mm to about 2 mm and hold a volume of about 1 microliter to about 50 microliters of liquid drug solution. The capillary volume is designed to produce a microtablet of predetermined weight and dimensions, taking into consideration the solids content of the liquid formulation, the tableting pressure, and the final density of the microtablet.

The tooling defining the capillary channels may be made of a metal or metal alloy, a ceramic, a glass, or silicon. The materials of construction and methods of fabrication are chosen to produce a smooth, well defined inner bore with relatively good heat transfer capability (preferable for the lyophilization process). Each capillary channel may be fabricated individually, for example where the channel is the bore of a separate glass or metal tube. Alternatively, an array of capillary channels may be created in unitary or multi-part block. For example, an array of capillary channels may be micro-machined into a silicon wafer. Alternatively, an array of holes may be conventionally machined into a block, such as one of 316 stainless steel, and then the holes electropolished to create an optimal surface finish.

In certain embodiments, the capillary ends may be coated with a hydrophobic material (such as wax or a hydrophobic silane coupling agent) to prevent the spreading of the formulation droplet on the end of the capillary. The capillary ends may be covered with a porous film or microscreen that would allow water sublimation during lyophilization, but would deter powder from escaping the capillary prior to tableting.

In one embodiment, the capillary channel walls are tapered to prevent the microtablet from skiving during ejection. In one embodiment, shown in FIG. 5A, the capillary tooling system includes a tube or block 500 having a capillary channel 502 with straight capillary channel walls (90 degrees to the bore diameter, "d"). This enables compression of the lyophilized drug formulation over the length. In another embodiment, shown in FIG. 5B, the capillary tooling system includes a tube or block 510 having a capillary channel 512 that includes tapered channel walls, which holds the compressed microtablet such that the bore diameter at the top of the channel, $d_1$, is greater than that the bottom of the channel, $d_2$, which may enable the compression and/or ejection forces to be reduced compared to the same system with straight, untapered capillary channel walls. For example, tapering the capillary wall by 0.25 degrees from the centerline circumferentially may reduce the ejection force required for ejecting the microtablet from the capillary.

Filling System

In one embodiment, the filling system includes an injection device or a dispensing device known in the art, such as a micropipette, hypodermic needle and syringe, or other suitable fluid transport and volume control equipment known for dispensing precise volumes of liquid. In another embodiment, filling may be accomplished by dipping the capillaries into the formulation and allowing the liquid to wick into the capillary. The outside of the capillaries may be made non-wetting, while the inner bore is made to wet to promote wicking of the liquid drug solution into the capillary channel. For example, silane coupling agents may be used to functionalize the outer surface of the capillary tube to make it non-wetting. Deposition processes and materials for non-wetting coatings are known to those skilled in the art. Vacuum infiltration may be used to aid the filling operation when the outside of the bore is non-wetting.

Compression System

The compression system may include one or more pistons and one or more actuators to drive the pistons into the lyophilization capillary channels or the compression capillary channels if used. In one embodiment, the compression system includes a pair of opposed pistons 106, 114, capable of being driven toward one another, with the lyophilized drug formulation sandwiched therebetween, in a single capillary channel as illustrated in FIG. 2A. In another embodiment, the compression system includes a single piston 206 capable of being driven toward a strike plate 207, with the lyophilized drug formulation sandwiched therebetween, in a single capillary channel as illustrated in FIG. 2B.

Figure 3A:
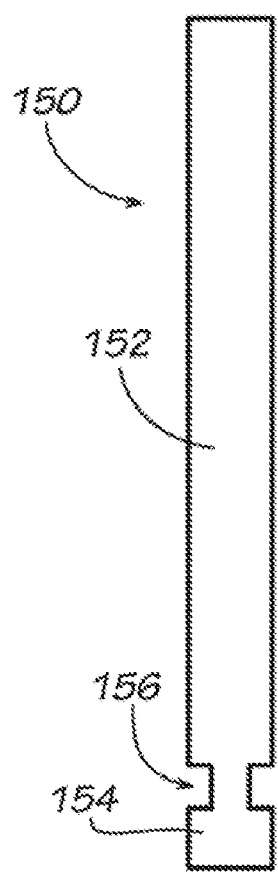
FIGS. 3A and 3B are cross-sectional views of a piston having a planar face (FIG. 3A) or concave face (FIG. 3B) according to the embodiments illustrated in FIGS. 2A and 2C, respectively.
Figure 3B:
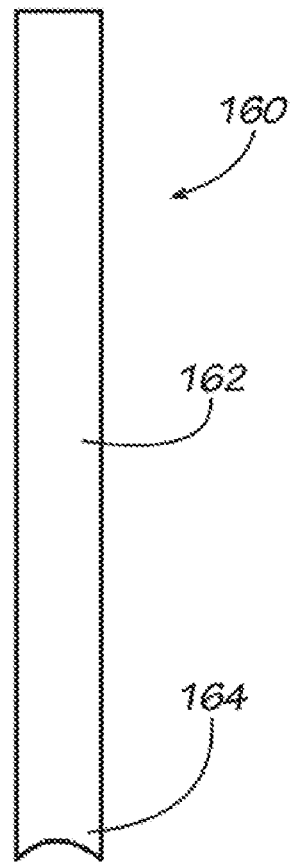

The piston used to compress the lyophilized drug formulation may have any suitable shape. For example, pistons 106 and 114 in FIG. 2A has a flat face for contacting/compressing the drug formulation. As another example pistons 206 and 306 in FIGS. 2B and 2C, respectively, have a concave face for contacting/compressing the drug formulation. Other contoured shapes are possible. FIGS. 3A and 3B show other possible variations of suitable piston shapes. In FIG. 3A, piston 150 has a cylindrical body 152 that has a flat-faced piston head 154 for contacting the lyophilized drug formulation and a groove relief structure 156. In FIG. 3B, piston 160 has a cylindrical body 162 that has a concave piston head 164 for contacting the lyophilized drug formulation and no groove relief structure. As shown in Example 2 below, the concave-face piston face may produce microtablets with less damage the drug contained therein, as compared to microtablets formed with a flat-faced piston.

Ejecting System

Essentially any suitable technique and devices may be used for ejecting the microtablet from the capillary channels. Desirably, the ejecting system is configured to gently discharge the microtablet so that it remains intact upon discharge. In various embodiments, the ejecting system includes a piston (either the same as or different than pistons used for compressing) and actuator, vibration means, a pressurized fluid (e.g., gas or liquid), gravity, or a combination thereof, which is effective to cause the microtablet to be discharged from an open end of the capillary channel. In other embodiments the ejecting system includes mechanisms, such as actuators, for unmating a first and second part of a two-part capillary tube or block of capillary channels.

C. Microtablet Formulations

The compositions of the liquid drug solution, the lyophilized drug formulation, and the compressed microtablets resulting from the liquid drug solution include at least one drug. The compositions also may include one or more pharmaceutically acceptable excipients.

Drug

The methods and systems described herein can be used with essentially any drug, or active pharmaceutical ingredient (API). In a preferred embodiment, the microtableting methods are specifically for use with potent biomolecules, such as proteins, antibodies, vaccines, RNA, DNA, or the like) without loss of activity. In other embodiments, the methodology can also be used for small molecule pharmaceuticals.

In one embodiment, the methods and systems are used to make microtablets comprising an anti-VEGF drug. Examples of such drugs include the antibody fragment ranibizumab/Lucentis™, the antibody bevacizumab/Avastin™, and the fusion protein aflibercept/Eylea™.

In one embodiment, the drug is a biomolecule and the composition for the controlled release of the biomolecule is a dispersible microtablet with a glassy amorphous matrix phase containing the drug and a combination of lyoprotectant, binding agent, buffer, surfactant, and/or slip agent excipients.

Excipients

Suitable excipients are known in the art. In certain embodiments, the compositions include lyoprotectants, binding agents, buffering agents, slip agents, and surfactants, which will aid the processing and handling of the microtablets. Other excipients may be used to enhance stability of the API and/or to control dissolution or release characteristics of the API in vivo. The excipient may be a non-volatile substance so that it is not removed during the lyophilization step of the process.

In one embodiment, the microtablet composition includes at least one lyoprotectant. For example, a glassy amorphous solid can be produced by lyophilizing a biomolecule API with a lyoprotectant. Examples of such lyoprotectants include trehalose, sucrose, mannitol, lactose, raffinose, sorbitol, and maltose. The specific lyoprotectant, and its concentration, will determine the glass transition (Tg) temperature of the lyophile. Generally, a ratio of >300:1 molar ratio of lyoprotectant:antibody is sufficient (See, e.g., Cleland et al, *J. Pharm. Sci,* 90:310-21 (2001)). Since moisture affects the Tg, the moisture content of the glassy amorphous matrix is preferably less than 1%, more preferably less than 0.5%. One skilled in the art can determine the ratio of lyoprotectant to drug.

A variety of binding agents known in the art may be used. In an embodiment, the lyoprotectant also provides drug binding properties to form the microtablet. For example, many sugars are routinely found in lyophilized parenterals and oral tablets; however, trehalose may preferred due to its high Tg, low hygroscopicity, good moldability and tablet hardness (See e.g., Ohtake & Wang, *J. Pharm. Sci.* 100:2020-53 (2011)). Binding agents with controllable swelling properties (upon hydration) are important, where little to no swelling is preferred. For example, a binding agent with low swelling is preferred to limit the mechanical stress on a drug delivery implant device, in which the microtablets may be loaded. Therefore, carboxymethyl cellulose would not be preferred in such embodiments.

Essentially any suitable pharmaceutically acceptable buffering agent, surfactant, or lubricant may be used. Examples of a suitable buffering agent include phosphate, citrate, acetate, histidine, glycine, or a combination thereof. The surfactant may be used to minimize interfacial denaturation in biomolecule solutions. In one embodiment, the surfactant comprises polysorbate 20 or 80 (e.g., less than 1%). Essentially any suitable pharmaceutically acceptable lubricant, slip or release agent may be used to facilitate release of the microtablets from the tools, to prevent adhesion of the microtablet to the fixture, and/or to facilitate ejection of the microtablet from the capillary channel. In one embodiment, the slip agent comprises magnesium stearate (e.g., less than 1%).

D. Use of Microtablets

The microtablets prepared herein may be used in numerous different drug delivery applications. A microtablet may be implanted in a patient directly by itself or the microtablet may be contained in an implantable controlled release delivery system, which may be inserted into the patient to provide local, regional, or systemic administration of drug. In one embodiment, the microtablets may be injected via a hollow needle or other administration device. For example, in certain embodiments the microtablets are suitable for drug delivery in ophthalmology (e.g., via direct intravitreal injection of microtablets or implantation of an implantable drug delivery device into the sclera, choroid, or other eye tissue or structure); subcutaneous drug delivery; drug delivery in the ear; drug delivery in or under the nails (e.g., for treatment of fungal infections); intra-tumoral drug delivery; or orthopedic drug delivery (including dental, joints and bone).

The present methods and compositions can be further understood and illustrated by the following non-limiting examples.

Example 1

A system was prepared using the prior art methods described in FIG. 1 to evaluate the weight variability and content uniformity of the tablets produced by a prior art coring process. An anti-VEGF antibody (bevacizumab) in the formulation Avastin was lyophilized (DURA freeze-drier from FTS Systems; the residual moisture in an adjacent trehalose cake was <1%) and lightly compressed (~2 psi) into a powder bed using the fixture described in FIG. 1. Tablets were cored from the cake using a 500 micron ID Fine Sciences coring tool. Tablets were cored and compressed against the strike plate at pressures between 5000 and 25,000 psi. Cored tablets were immediately ejected and weighed using a Mettler Toledo MT5 microbalance.

Comparative experiments were conducted using exemplary embodiments of the capillary tooling systems and methods described herein. Glass capillaries with a bore diameter of 0.46 mm and a length of 16 mm were filled with 2.6 µL of Avastin and lyophilized using the same DURA freezer-drier from FTS systems as described above. The lyophilizate was compressed in the lyophilization capillary with a 0.450 mm diameter piston at pressures between 5,000 and 20,000 psi.

Figure 9A:
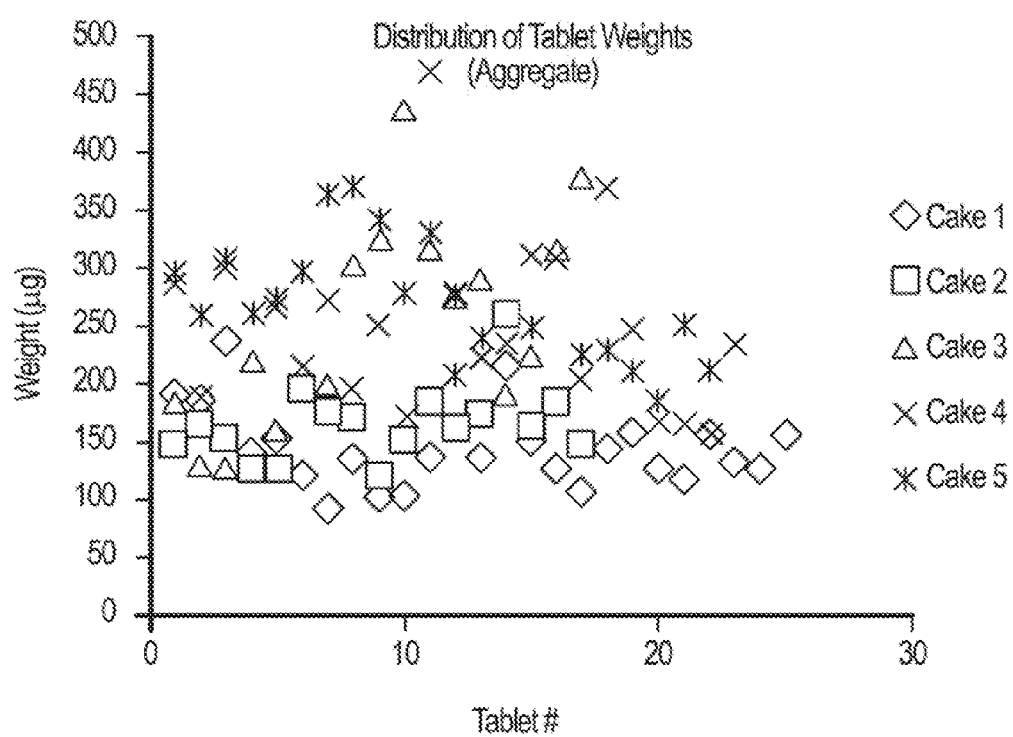
FIGS. 9A and 9B are graphs showing the aggregate distribution of table weights for tablets produced using a prior art coring method (FIG. 9A) or using an exemplary embodiment of the microtableting methods described herein (FIG. 9B).
Figure 9B:
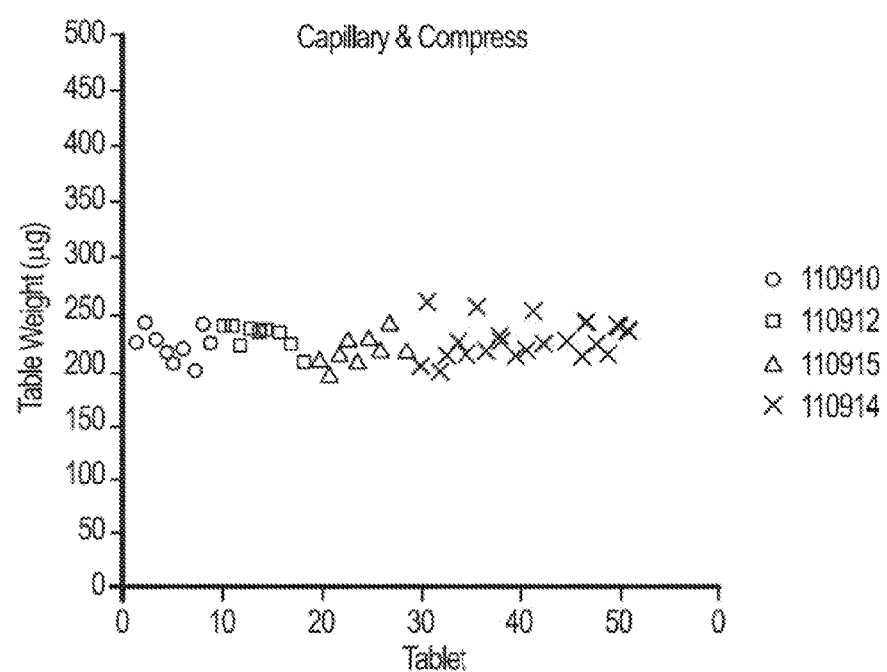

The results of these experiments are illustrated in FIGS. 9A and 9B, which show the aggregate distribution of tablet weights for tablets produced from five different powder beds (cakes) using the prior art coring method (9A) and the aggregate distribution of tablet weights for tablets produced from four different runs using an exemplary method and capillary system (9B). As can be seen from the data, there was a significant variation in the tablet weights in the prior art method, indicating there also would be a significant variation in the effective dose of each tablet. Conversely, there was no significant variation in the tablet weights in the exemplary method of the methods and systems described herein, indicating that there would be significantly less variation in the effective dose of each tablet.

Example 2

Experiments were conducted to determine the effect the shape of the piston face has on the resulting microtablet. Approximately 2 µL of Avastin was filled into glass capillaries using the capillary tooling system illustrated in FIG. 2B and lyophilized. The lyophylisate was then compressed into tablets in the glass capillaries using a piston having a flat tip (FIG. 3A) or a concave tip (FIG. 3B). The tableting pressure was kept constant at approximately 8,000 psi for all samples.

Each tablet produced was divided in half with one side of the top half having contacted the tableting piston and one side of the bottom half having contacted the strike plate.

A measurement of turbidity was used to analyze the divided microtablet portions. A higher turbidity is associated with unwanted modification of, or damage to the API. The turbidity was quantified by re-dissolving tablet portions in phosphate buffered saline and measuring the absorbance at 350 nm. The reported absorbance reading was normalized to 1 mg/mL of Bevacizumab and a 1 cm absorbance length. For reference, normalized absorbance values below 0.07 are considered clear solutions. The results are shown in the table below.

| Sample | Normalized Absorbance (350 nm) | Tablet Half | Piston Tip Shape |
|---|---|---|---|
| 1 | 0.05 | Bottom | Flat |
| 2 | 0.08 | Top | Flat |
| 3 | 0.05 | Bottom | Flat |
| 4 | 0.18 | Top | Flat |
| 5 | 0.03 | Bottom | Concave |
| 6 | 0.04 | Top | Concave |
| 7 | 0.04 | Bottom | Concave |
| 8 | 0.04 | Top | Concave |

The results indicate that the tablet portion in contact with the piston ("Top" portion) have a consistently higher turbidity than the tablet portion not in contact with the piston ("Bottom" portion). The results further suggested, however, that the use of a concave-shaped piston face reduced the turbidity significantly and that there was very little difference between the turbidity of these tablet portions. Not wishing to be bound by any theory, it is believed that the shape of the piston-API interface affects the distribution of forces during the compression of the microtablet. The flat-shaped piston tip may have damaged the API due to concentrated compression forces at the interface, whereas the concave-shaped piston tip more evenly distributed the compression forces at the interface, thereby minimizing the damage to the API during the compression step.

This disclosure is illustrative and not limiting. Further modifications will be apparent to one skilled in the art in light of this disclosure and such modifications are intended to fall within the scope of the appended claims. Each publication and patent application cited in the specification is incorporated herein by reference in its entirety as if each individual publication or patent application were specifically and individually put forth herein.

We claim:

1. A system for making a drug microtablet comprising:
   a capillary tooling system having at least one lyophilization capillary channel;
   a liquid dispensing device operable to load a liquid drug solution into the at least one lyophilization capillary channel;
   a freeze-dryer operable to lyophilize the liquid drug solution in the at least one lyophilization capillary channel and produce a lyophilized drug formulation therein; and
   a compression device operable to compress the lyophilized drug formulation in the at least one lyophilization capillary channel, or in at least one compression capillary channel, to form a microtablet.

2. The system of claim 1, wherein the capillary tooling system comprises a plurality of the lyophilization capillary channels defined directly in a single block fixture.

3. The system of claim 1, wherein the capillary tooling system comprises two or more capillary tubes, each tube being disposed in one of an array of wells or slots and each capillary tube having a single lyophilization capillary channel.

4. The system of claim 3, wherein the capillary tubes are formed of metal or glass and the array of microwells is defined in a metal block fixture.

5. The system of claim 1, wherein the compression device comprises at least one piston and an actuator to drive the at least one piston into the at least one lyophilization capillary channel or in the at least one compression capillary channel.

6. The system of claim 1, which is configured to compress the lyophilized drug formulation in the at least one lyophilization capillary channel to form the microtablet.

7. The system of claim 1, which is configured to compress the lyophilized drug formulation in the at least one compression capillary channel to form the microtablet.

8. The system of claim 1, further comprising an ejector system operable to transfer the lyophilized drug formulation directly from the lyophilization capillary channel to the compression capillary channel before the lyophilized drug formulation is compressed to form the microtablet.

9. The system of claim 8, wherein the diameter of the compression capillary channel is from 10% to 70% larger than the diameter of the lyophilization capillary channel.

10. The system of claim 1, wherein the lyophilization or compression capillary channel is defined in a tooling block which comprises:
    a first part having a first mating face having a straight groove therein, and a second part having a second mating face having a straight groove therein, wherein the first and second mating faces are configured to mate together such that the groove of the first part is positioned adjacent and aligned with the groove of the second part to define the lyophilization or compression capillary channel.

11. The system of claim 1, wherein the compression device is operable to compress the lyophilized drug formulation with a predetermined force for a period from about one second to about 600 seconds.

12. The system of claim 1, wherein the compression device is operable to compress the lyophilized drug formulation by application of a predetermined force from about 1,000 psi to about 30,000 psi.

13. The system of claim 1, which is configured to produce the microtablet having a largest dimension from 50 microns to 2000 microns.

14. The system of claim 1, wherein the lyophilization capillary channel has an aspect ratio of between 10 and 100.

15. The system of claim 1, wherein the lyophilization capillary channel has a diameter between 100 µm and 1000 µm.

16. The system of claim 1, wherein the lyophilization or compression capillary channel is tapered to facilitate ejection of the microtablet.

17. A system for making a drug microtablet comprising:
a capillary tooling system having at least one lyophilization capillary channel;
a liquid dispensing device operable to load a liquid drug solution into the at least one lyophilization capillary channel;
a freeze-dryer operable to lyophilize the liquid drug solution in the at least one lyophilization capillary channel and produce a lyophilized drug formulation therein; and
a compression device operable which comprises at least one piston and an actuator to drive the at least one piston into the at least one lyophilization capillary channel or in the at least one compression capillary channel, to compress the lyophilized drug formulation in the at least one lyophilization capillary channel, or in at least one compression capillary channel, to form a microtablet.

18. The system of claim 17, wherein the piston comprises a concave face for contacting the lyophilized drug formulation.

19. The system of claim 17, wherein the lyophilization capillary channel has an aspect ratio of between 10 and 100.

20. The system of claim 17, wherein the lyophilization capillary channel has a diameter between 100 µm and 1000 µm.

* * * * *